(12) United States Patent
Fantini

(10) Patent No.: US 11,426,129 B2
(45) Date of Patent: Aug. 30, 2022

(54) COHERENT HEMODYNAMICS SPECTROSCOPY AND MODEL BASED CHARACTERIZATION OF PHYSIOLOGICAL SYSTEMS

(71) Applicant: Trustees of Tufts College, Medford, MA (US)

(72) Inventor: Sergio Fantini, Winchester, MA (US)

(73) Assignee: Trustees of Tufts College, Medford, MA (US)

( * ) Notice: Subject to any disclaimer, the term of this patent is extended or adjusted under 35 U.S.C. 154(b) by 1293 days.

(21) Appl. No.: 14/654,133

(22) PCT Filed: Oct. 21, 2013

(86) PCT No.: PCT/US2013/065907
§ 371 (c)(1),
(2) Date: Jun. 19, 2015

(87) PCT Pub. No.: WO2014/099124
PCT Pub. Date: Jun. 26, 2014

(65) Prior Publication Data
US 2015/0366514 A1 Dec. 24, 2015

Related U.S. Application Data

(60) Provisional application No. 61/740,534, filed on Dec. 21, 2012.

(51) Int. Cl.
*A61B 5/02* (2006.01)
*A61B 5/0205* (2006.01)
(Continued)

(52) U.S. Cl.
CPC .......... *A61B 5/7278* (2013.01); *A61B 5/0075* (2013.01); *A61B 5/02028* (2013.01);
(Continued)

(58) Field of Classification Search
None
See application file for complete search history.

(56) References Cited

U.S. PATENT DOCUMENTS 5,810,010 A * 9/1998 Anbar .................... A61B 5/015
600/407
6,049,727 A 4/2000 Crothall
(Continued)

FOREIGN PATENT DOCUMENTS

WO 2011/103102 8/2011

OTHER PUBLICATIONS

Britton Chance, Optical Method, 1991, Annu. Rev. Biophys. Chem, 20, pp. 1-28.*

(Continued)

*Primary Examiner* — Etsub D Berhanu
(74) *Attorney, Agent, or Firm* — Occhiuti & Rohlicek LLP

(57) ABSTRACT

A method for inferring characteristics of a physiological system includes measuring one or more physiological signals in the physiological system and inferring characteristics of the physiological system from the one or more measured physiological signals using a multiple vascular compartment hemodynamic model, the multiple vascular compartment hemodynamic model defining a relationship between the one or more measured physiological signals and the characteristics of the physiological system. When the one or more measured physiological signals include coherent oscillations at a plurality of frequencies, the method is termed coherent hemodynamics spectroscopy. The multiple vascular compartment hemodynamic model is based on an average time spent by blood in one or more of said vascular compartments and a rate constant of oxygen diffusion.

27 Claims, 7 Drawing Sheets

(51) Int. Cl.
    *A61B 5/145*     (2006.01)
    *A61B 5/00*     (2006.01)
    *A61B 5/1455*     (2006.01)
    *A61B 5/026*     (2006.01)

(52) U.S. Cl.
    CPC ........ *A61B 5/0263* (2013.01); *A61B 5/14542* (2013.01); *A61B 5/14551* (2013.01); *A61B 5/4064* (2013.01); *A61B 5/7257* (2013.01)

(56) References Cited

U.S. PATENT DOCUMENTS

| | | | |
|---|---|---|---|
| 6,155,976 | A | 12/2000 | Sackner et al. |
| 2006/0287600 | A1 | 12/2006 | McEowen |
| 2007/0195330 | A1* | 8/2007 | Ohashi ............... A61B 5/14551 356/498 |
| 2007/0293760 | A1 | 12/2007 | Schaafsma |
| 2010/0030062 | A1 | 2/2010 | Bolar et al. |
| 2011/0169978 | A1* | 7/2011 | Lasser .................. A61B 3/1233 348/222.1 |

OTHER PUBLICATIONS

Ying Zheng, A three-compartment model of the hemodynamic response and oxygen delivery to brain, Jan. 17, 2005, NeuroImage, 28, pp. 925-939.*

Hellmuth Obrig, Spontaneous Low Frequency Oscillations of Cerebral Hemodynamics and Metabolism in Human Adults, 2000, NeuroImage, 12, pp. 623-639 (Year: 2000).*

Maria Angela Franceschini, Near-Infrared spiroximetryL noninvasive measurements of venous saturation in piglets and human subjects, 2002, J Appl Physiol, 92, pp. 372-384 (Year: 2002).*

Cheng et al. Noninvasive optical evaluation of spontaneous low frequency oscillations in cerebral hemodynamics. NeuroImage 62 (2012) 1445-1454. (Year: 2012).*

Pierro et al. Phase characterization of oscillatory components of the cerebral concentrations of the cerebral concentrations of oxy-hemoglobin and deoxy-hemoglobin. Proceedings of SPIE. (Year: 2011).*

Katura et al. Quantitative evaluation of interrelations between spontaneous low-frequency oscillations in cerebral hemodynamics and systemic cardiovascular dynamics. NeuroImage 31 (2006) 1592-1600. (Year: 2006).*

Sassaroli et al. Low-Frequency Spontaneous Oscillations of Cerebral Hemodynamics Investigated with Near-Infrared Spectroscopy: A Review. IEEE Journal of Selected Topics in Quantum Electronics, vol. 18, No. 4, Jul./Aug. 2012. (Year: 2012).*

Schytz et al. Spontaneous Low-Frequency Oscillations in Cerebral Vessels: Applications in Carotid Artery Disease and Ischemic Stroke. J Stroke Cerebrovasc Disc. 2010; 19(6): 465-474. (Year: 2010).*

Desjardins, et al., "Application of a Multicompartment Dynamical Model to Multimodal Optical Imaging for Investigating Individual Cerebrovascular Properties," Optical Sensing II, vol. 7171, Feb. 12, 2009, pp. 717109-717114.

Huppert et al., "A Multicompartment Vascular Model for Inferring Baseline and Functional Changes in Cerebral Oxygen Metabolism and Arterial Dilation," Journal of Brlood Flow & Metabolism, (2007) 27, 1262-1279.

Zheng et al., "A Three-Compartment Model of the Hemodynamic Response and Oxygen Deliveiy to Brain," NeuroImage, 28 (2005) 925-939.

* cited by examiner

| Physiological quantity | Symbol | Steady State | Dynamic |
|---|---|---|---|
| Hemoglobin concentration in blood | ctHb | • | |
| Arterial Saturation | $S^{(a)}$ | • | |
| Rate constant for oxygen diffusion | $\alpha$ | • | |
| Capillary blood transit time | $t^{(c)}$ | • | |
| Venous blood transit time | $t^{(v)}$ | • | |
| Arterial blood volume | $CBV_0^{(a)}$ | • | |
| Capillary blood volume | $F^{(c)}CBV_0^{(c)}$ | • | |
| Venous blood volume | $CBV_0^{(v)}$ | • | |
| Maximum amplitude ratio of flow-to-volume oscillations | $k$ | • | |
| Cutoff frequency for autoregulation | $\omega_c$ | • | |
| Blood volume phasor | cbv$(\omega)$ | | • |

FIG. 5

| Physiological quantity | Symbol | Steady State | Dynamic |
|---|---|---|---|
| Hemoglobin concentration in blood | ctHb | • | |
| Arterial Saturation | $S^{(a)}$ | • | |
| Rate constant for oxygen diffusion | $\alpha$ | • | |
| Capillary blood transit time | $t^{(c)}$ | • | |
| Venous blood transit time | $t^{(v)}$ | • | |
| Arterial blood volume | $CBV_0^{(a)}$ | • | |
| Capillary blood volume | $F^{(c)}CBV_0^{(c)}$ | • | |
| Venous blood volume | $CBV_0^{(v)}$ | • | |
| Time-varying blood volume | $cbv(t)$ | | • |
| Difference between the time-varying blood flow and the time-varying cerebral metabolic rate of oxygen | $cbf(t) - cmro_2(t)$ | | • |

FIG. 7

COHERENT HEMODYNAMICS SPECTROSCOPY AND MODEL BASED CHARACTERIZATION OF PHYSIOLOGICAL SYSTEMS

CROSS-REFERENCE TO RELATED APPLICATIONS

This application is a National Stage of International Application No. PCT/US2013/065907 filed on Oct. 21, 2013, which claims the benefit of U.S. Provisional Application No. 61/740,534 filed Dec. 21, 2012 the contents of which are hereby incorporated by reference in their entirety.

STATEMENT AS TO FEDERALLY SPONSORED RESEARCH

This invention was made with government support under grant MH093846 awarded by The National Institutes of Health. The government has certain rights in the invention.

BACKGROUND

This invention relates to the diagnosis and monitoring of medical disorders and a variety of physiological and functional conditions.

The medical diagnosis and monitoring of physical disorders and, in particular, brain disorders can be difficult due to the sensitivity of brain tissue to invasive medical probes and procedures. For this reason, techniques have been developed to non-invasively measure physiological characteristics of brain tissue for the purpose of non-invasive diagnosis and monitoring of brain disorders. For example, some hemodynamic-based neuroimaging studies utilize technologies such as functional near infra-red spectroscopy (fNIRS) and functional magnetic resonance imaging (fMRI) to measure and collect data related to the temporal response of blood flow and tissue oxygenation to brain activation. The collected data is analyzed to diagnose and monitor brain disorders.

Some previous approaches analyze the collected data using models (e.g., abstractions based on mathematical equations governing quantities representing physiological systems) of cerebral hemodynamics and oxygen supply. For example, hemodynamic based neuroimaging techniques such as functional near-infrared spectroscopy (fNIRS) and functional magnetic resonance imaging (fMRI) depend on hemodynamic models to relate the signals that they measure to the underlying physiological and functional processes of interest. In the past, efforts have been made to develop successful quantitative abstractions of the complex cerebral vasculature, blood flow, oxygen supply, and their dynamic perturbations associated with brain function or with a variety of physiological challenges. In general, the major challenge faced by such quantitative abstractions, or mathematical models, is the achievement of an acceptable compromise between avoiding over-simplification of cerebral hemodynamics and oxygen transport processes, while limiting the number of free parameters included in the model. The approach to this problem has typically been based on modeling the cerebral vasculature with electrical or hydrodynamics equivalent circuits. Some of these previous approaches have been successful and have found broad applicability in the fields of fMRI and fNIRS. However, the previous approaches must necessarily introduce a number of limiting approximations to the complex and highly variable structure of the microvascular cerebral network. At a cost of increasing the complexity of the mathematical models, efforts to describe multiple vascular compartments or dynamic autoregulatory processes have resulted in a large number of free parameters to describe such increasingly complex anatomical or physiological conditions.

SUMMARY

In a general aspect of the invention, an approach to collecting and analyzing hemodynamic data on human tissue in vivo allows extraction of functional, physiological, and metabolic information on the tissue. The approach includes inducing or enhancing coherent hemodynamic oscillations by means of predetermined periodic physiological maneuvers (e.g., paced breathing, repeated squat-stand maneuvers, lying on a bed that periodically tilts, inflating/deflating pneumatic cuffs around the limbs, cyclic brain activation, modulation of the fraction of inspired carbon dioxide ($FiCO_2$), etc.). However, spontaneous cerebral hemodynamic oscillations featuring a sufficient level of coherence are also suitable for the methods described herein. Dynamic data on the concentrations of oxy-hemoglobin and deoxy-hemoglobin in tissue are collected (e.g., with near-infrared spectroscopy). In the time domain, the collected data are analyzed according to a hemodynamic perturbation model to predict functional, physiological, or metabolic information (e.g., the assessment of local cerebral autoregulation, the determination of the hemodynamics and metabolic changes associated with brain activity, mapping of functional connectivity in the brain, etc.). In the frequency domain, the hemodynamic perturbation model yields an analytical solution based on a phasor representation of the collected data that allows for quantitative spectroscopy of coherent hemodynamic oscillations. This technology is termed "coherent hemodynamics spectroscopy" (CHS) and can be used to assess cerebral autoregulation and to study hemodynamic oscillations resulting from a variety of periodic physiological challenges, brain activation protocols, or physical maneuvers.

In general, any data collection/measurement technique that is capable of measuring the concentration and oxygenation of hemoglobin in tissue can benefit from the approach.

In a general aspect, a method for inferring characteristics of a physiological system includes measuring one or more physiological signals in the physiological system, and inferring characteristics of the physiological system from the one or more measured physiological signals using a multiple vascular compartment hemodynamic model, the multiple vascular compartment hemodynamic model defining a relationship between the one or more measured physiological signals and the characteristics of the physiological system. The multiple vascular compartment hemodynamic model is based on an average time spent by blood in one or more of said vascular compartments and a rate constant of oxygen diffusion.

Aspects may include one or more of the following features.

The one or more measured physiological signals may include coherent oscillations at a plurality of frequencies and the method may further include determining spectral representations of the one or more measured physiological signals wherein inferring the characteristics of the physiological system from the one or more measured physiological signals using the multiple vascular compartment hemodynamic model includes inferring the characteristics based on the spectral representations of the one or more measured physiological signals. The coherent oscillations at the plurality of frequencies in the physiological system may occur spontaneously.

The coherent oscillations at the plurality of frequencies in the physiological system may be induced by subjecting an organism including the physiological system to a plurality of periodic protocols, each periodic protocol of the plurality of periodic protocols having a period corresponding to one of the frequencies of the plurality of frequencies. The plurality of periodic protocols may include one or more of: paced breathing, repeated active exercise maneuvers, repeated passive exercise maneuvers, periodic tilting bed procedures, cyclic inflation and deflation of a pneumatic device, cyclic brain activation, and modulation of the fraction of inspired oxygen ($FiO_2$) or carbon dioxide ($FiCO_2$).

The coherent oscillations at the plurality of frequencies in the physiological system may be induced by subjecting an organism including the physiological system to a perturbation. The perturbation may include a sudden change applied to the organism including the physiological system.

Inferring the characteristics based on the spectral representation of the one or more measured physiological signals may include fitting the spectral representation of the measured physiological signals to the multiple vascular compartment hemodynamic model. The one or more measured physiological signals may include temporal varying physiological signals and inferring the characteristics of the physiological system from the one or more measured physiological signals using the multiple vascular compartment hemodynamic model may include inferring time varying characteristics of the physiological system.

The one or more physiological signals may be measured using near-infrared spectroscopy (NIRS) or functional near-infrared spectroscopy (fNIRS) techniques. The one or more physiological signals may be measured using functional magnetic resonance imaging (fMRI) techniques. The physiological system may be a brain autoregulation system. The physiological system may be a cerebrovascular reactivity system. The physiological system may be a cerebral blood volume system. The physiological system may be a cerebral blood flow system. The physiological system may be a cerebral metabolic rate of oxygen system.

In another aspect, in general, a method for inferring characteristics of a physiological system includes measuring one or more physiological signals in the physiological system, wherein the one or more measured physiological signals include coherent oscillations at a plurality of frequencies, determining spectral representations of the one or more measured physiological signals, and inferring characteristics of the physiological system from the spectral representations of the one or more measured physiological signals based on previously determined correlations between the characteristics of the physiological system and individual features of the spectral representations of the one or more measured physiological signals.

Aspects may include one or more of the following features.

The coherent oscillations at the plurality of frequencies in the physiological system may occur spontaneously. The coherent oscillations at the plurality of frequencies in the physiological system may be induced by subjecting an organism including the physiological system to a plurality of periodic protocols, each periodic protocol of the plurality of periodic protocols having a period corresponding to one of the frequencies of the plurality of frequencies. The plurality of periodic protocols may include one or more of: paced breathing, repeated active exercise maneuvers, repeated passive exercise maneuvers, periodic tilting bed procedures, cyclic inflation and deflation of a pneumatic device, cyclic brain activation, and modulation of the fraction of inspired oxygen (FiO2) or carbon dioxide (FiCO2). The coherent oscillations at the plurality of frequencies in the physiological system may be induced by subjecting an organism including the physiological system to a perturbation. The perturbation may include a sudden change applied to the organism including the physiological system.

In another aspect, in general, a system for inferring characteristics of a physiological system includes a measurement module for measuring one or more physiological signals in the physiological system; and an inference module for inferring characteristics of the physiological system from the one or more measured physiological signals using a multiple vascular compartment hemodynamic model, the multiple vascular compartment hemodynamic model defining a relationship between the one or more measured physiological signals and the characteristics of the physiological system. The multiple vascular compartment hemodynamic model is based on an average time spent by blood in one or more of said vascular compartments and a rate constant of oxygen diffusion.

Aspects may have one or more of the following advantages.

Among other advantages, the hemodynamic perturbation model treats the complex microvasculature as a whole, without making assumptions about its detailed architecture, and without introducing a large number of parameters to describe it. Thus, an advantageous compromise is made, sufficiently describing the complexity of the microvasculature while making use of a limited number of free parameters. Furthermore, the hemodynamic perturbation model utilizes a new frequency-resolved measurement scheme that opens up a new technical avenue that may find numerous applications in the design of new instrumental techniques and in a number of research and clinical areas.

The hemodynamic perturbation model described above is capable of predicting data representative of localized cerebral autoregulation and cerebrovascular reactivity. This is an improvement over conventional measurement systems which rely on inferring data representative of global cerebral autoregulation and cerebrovascular reactivity based on a systemic measurement of arterial blood pressure (e.g., by finger plethysmography) and a global cerebral measurement of blood flow (e.g., by transcranial Doppler ultrasound on the middle cerebral artery).

The model described above aims to model the tissue concentration and oxygen saturation of hemoglobin. Such a model is immediately relevant to existing measurement technologies such as fMRI and fNIRS.

The hemodynamic model accounts for the complexity of the cerebral vascular network on the basis of a small number of physiological parameters.

Other features and advantages of the invention are apparent from the following description, and from the claims.

DESCRIPTION OF DRAWINGS

FIG. 5 is a list of physiological parameters considered by the inference system of FIG. 4.

FIG. 7 is a list of physiological parameters considered by the inference system of FIG. 6.

DESCRIPTION

1 Overview

Figure 1:
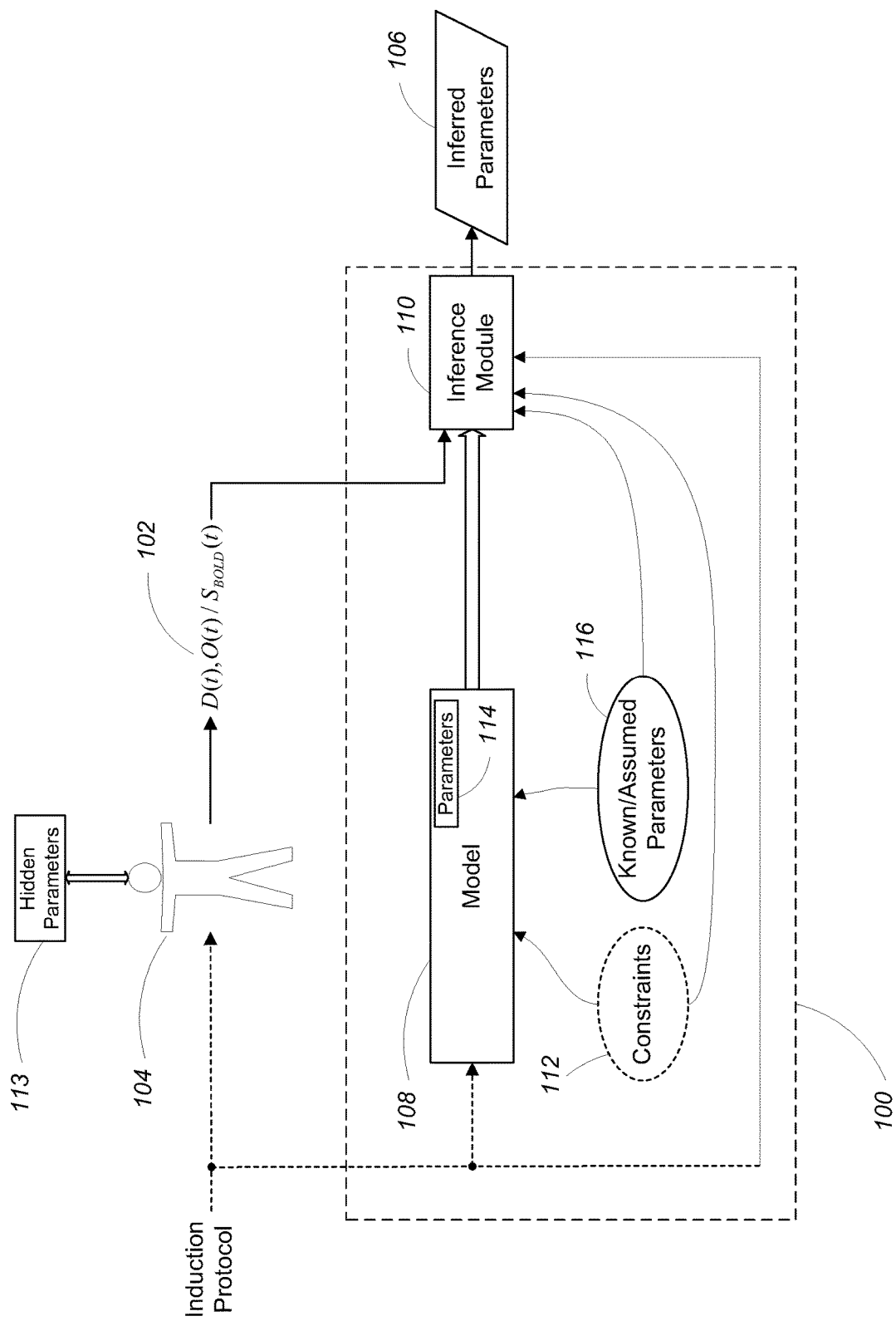
FIG. 1 is a generalized cerebral hemodynamics and oxygen supply model based inference system.

Referring to FIG. 1, in a use of an embodiment of the approach, a test subject 104 is connected to a cerebral hemodynamic and oxygen supply modeling system 100. Physiological aspects of the test subject 104 are associated with a number of physiological parameters 113 which characterize the baseline and dynamic behavior of hemodynamics and oxygen supply in the test subject's brain. The physiological parameters 113 include valuable clinical information which medical professionals can use as a basis for diagnosing or monitoring the test subject 104. However, the physiological parameters 113 are not directly observable using conventional medical technologies. That is, the physiological parameters 113 are "hidden parameters."

As an alternative to directly measuring the physiological parameters 113, the cerebral hemodynamic and oxygen supply modeling system 100 is configured to receive one or more measured physiological signals 102 (e.g., from a hemoglobin concentration and oxygenation sensor—not shown) which are observable from the test subject 104 and to process the physiological signals 102 to infer an estimate of the hidden physiological parameters 113 (i.e., a set of inferred parameters 106). In general, the physiological signals 102 are signals that are related to the hidden physiological parameters 113 and can be measured using neuroimaging techniques such as fNIRS or fMRI. For example, the physiological signals 102 may include: a tissue concentration of deoxy-hemoglobin (D(t)), a tissue concentration of oxy-hemoglobin (O(t)), and/or an fMRI BOLD signal ($S_{BOLD}$).

To generate the estimate of the hidden physiological parameters 113, the system 100 includes a hemodynamic and oxygen supply model 108 and a parameter inference module 110. As is described in greater detail below, the model 108 is a three compartment hemodynamic model which defines analytical relationships between the physiological signals 102 and the hidden physiological parameters 113. The inference module 110 receives the physiological signals 102 and generates the inferred physiological parameters 106 based on the model 108. In some examples, the inference module 110 uses the model 108 to infer hidden physiological baseline parameters (i.e., physiological parameters which remain constant over time) using a frequency-domain implementation. In other examples, the inference module 110 uses the model 108 to infer hidden dynamic functional parameters (i.e., parameters which vary over time) using a time-domain implementation. Depending on which of the hidden physiological parameters 113 are to be inferred, the model 108 may be associated with a specific set of known or assumed model parameter values 116 and in some examples, a specific set of model parameter constraints 112.

In some examples, the test subject 104 is instructed to perform or is subjected to one or more induction protocols. In some examples, the induction protocols are periodic in nature (e.g., paced breathing, cyclic inflation of a pneumatic thigh cuff, etc.) while in other examples the induction protocols are non periodic in nature (e.g., a step function-like maneuver such as the sudden deflation of an inflated pneumatic thigh cuff). The effect of the induction protocol can be modeled as providing an input to the model of the physiological system.

2 Cerebral Hemodynamic and Oxygen Supply Model

Before delving into the details of how the model is used to infer the hidden physiological parameters, an introduction to the three compartment cerebral hemodynamic and oxygen supply model is presented. Very generally, the hemodynamic model relates measured physiological signals (e.g., fNIRS and fMRI signals) to a set of steady state and dynamic parameters that characterize the cerebral blood volume, blood flow, and metabolic rate of oxygen.

Figure 2:
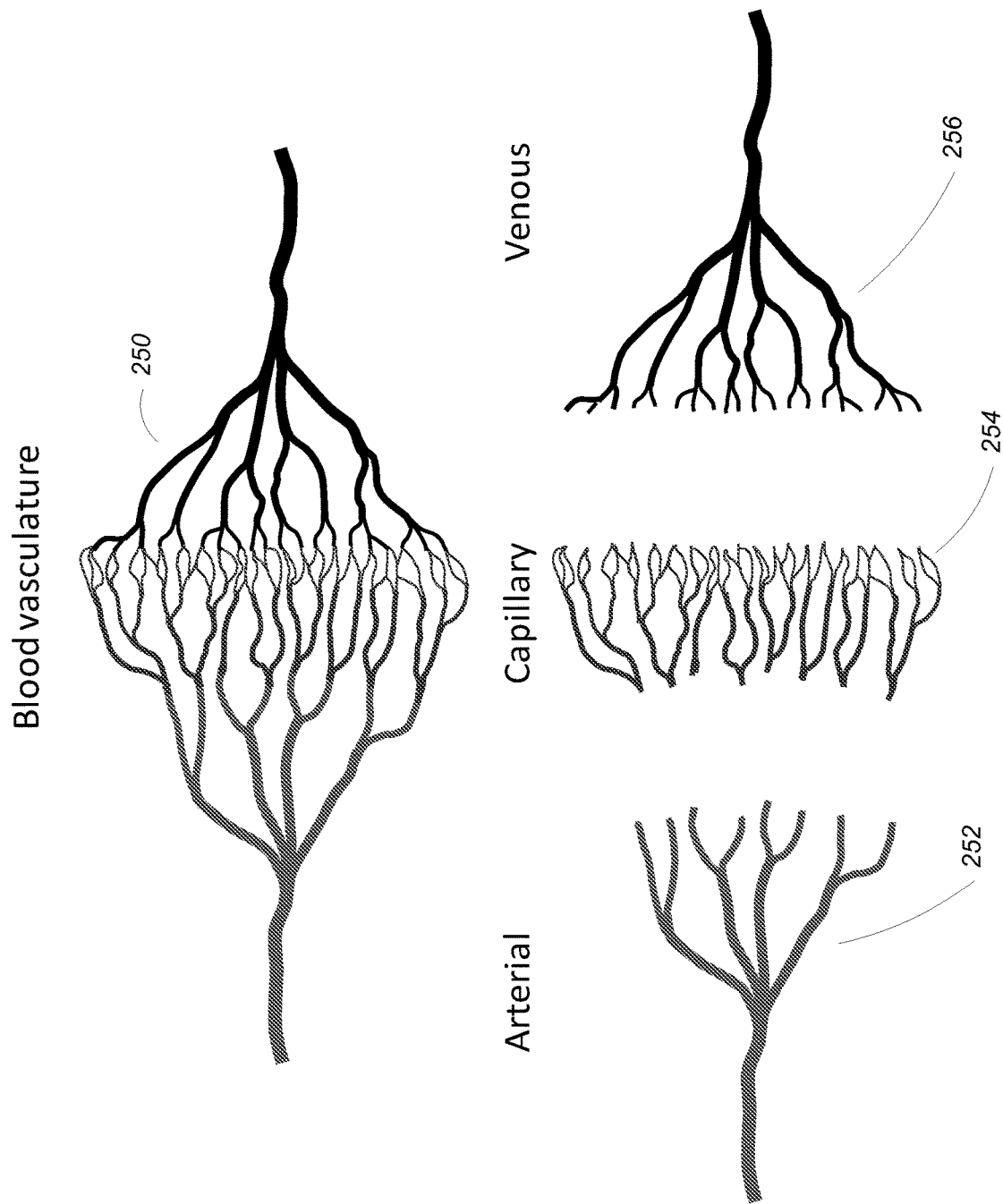
FIG. 2 is a simplified representation of blood vasculature.

Referring to FIG. 2, a simplified example of blood vasculature 250 can be abstracted into three separate compartments: an arterial compartment 252, a capillary compartment 254, and a venous compartment 256. In general, the arterial compartment 252 is not significantly involved in the diffusion of oxygen to tissue, it does not feature a longitudinal oxygen gradient, and its blood oxygenation is unaffected by changes in flow velocity and oxygen consumption. For all vascular compartments 252, 254, and 256 the tissue concentration of hemoglobin is only affected by volume changes. The capillary compartment 254 is the only compartment from which the significant diffusion of oxygen to tissue occurs (i.e., from small arterioles and capillaries). Thus, in the capillary compartment 254, the interplay between blood flow velocity and oxygen consumption induces changes in the blood concentrations of oxy-hemoglobin and deoxy-hemoglobin.

The basis of the model is to separately consider the arterial, capillary, and venous vascular compartments in the brain, knowing that each individual red blood cell in the blood stream will travel sequentially through these three compartments and will spend a certain average time in the capillary and venous compartments, $t^{(c)}$ and $t^{(v)}$ respectively. In this approach, the complexity and inter-subject variability of the vascular network architecture does not have to be considered because the most important factor is the average time that each red blood cell (and all of its hemoglobin molecules) spends in each compartment. The oxygen transfer from blood to tissue, which takes place in the capillary compartment, is described by a single rate constant for oxygen diffusion, a, so that the deoxygenation (or desaturation) of hemoglobin in the capillary compartment is fully determined by a and $t^{(c)}$. The model quantitatively describes the desaturation of hemoglobin as it flows through the capillary compartment, and determines how such dynamic desaturation is affected by changes in the blood flow velocity and the rate of oxygen diffusion.

Figure 3:
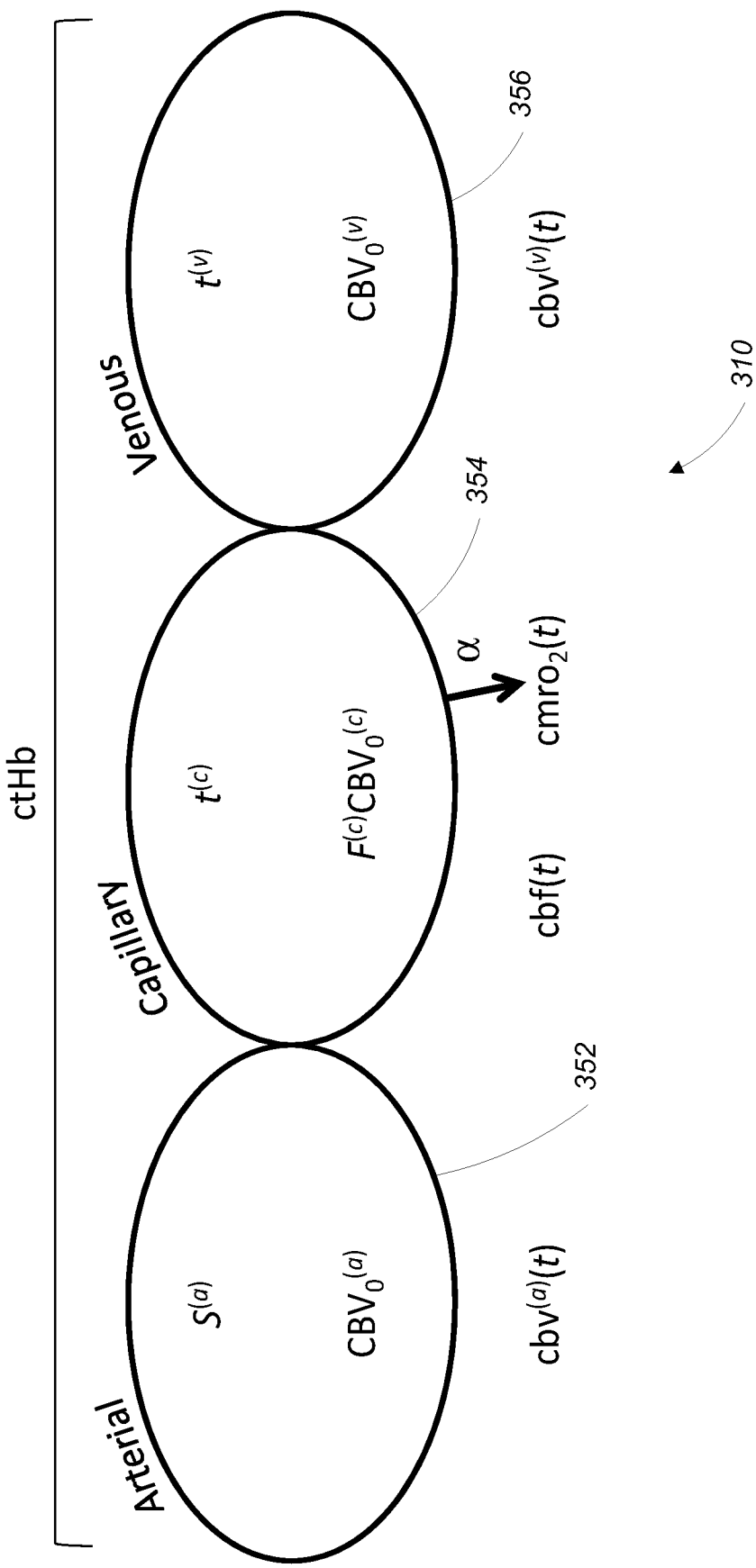
FIG. 3 is a diagram of a cerebral hemodynamics and oxygen supply model.

Referring to FIG. 3, one example of the hemodynamic perturbation model 310 for modeling tissue including the vasculature of FIG. 2 is shown. In general, the model 310 quantifies a temporal evolution of the concentration and oxygen saturation of hemoglobin in tissue (i.e., concentrations of oxy-hemoglobin, deoxy-hemoglobin, total hemoglobin, and hemoglobin saturation) as determined by both steady state and time-varying hemodynamic and metabolic parameters such as blood volume, flow velocity, and oxygen consumption. The model 310 is configured to determine separate contributions from arterioles, capillaries, and venules that comprise the tissue microvasculature, and treats them as a complete network without making any assumptions on the details of the architecture and morphology of the microvascular bed. A key role in the model is played by the effective blood transit time through the capillaries and its associated probability of oxygen release from hemoglobin to tissue, as described by a rate constant for oxygen diffusion.

Being based on the abstracted blood vasculature of FIG. 2, the model 310 includes three compartments: an arterial compartment 352, a capillary compartment 354, and a venous compartment 356. The overall model 310 and each of the compartments 352, 354, 356 included in the model are associated with a number of predefined model parameters. In general, there are two types of model parameters: steady state "physiological baseline parameters" and time-varying "dynamic functional parameters."

2.1 Steady State Physiological Baseline Parameters

The steady state physiological baseline parameters are parameters that are assumed to remain constant over time. For example, according to the rate constant for oxygen diffusion, as blood flows through the capillary compartment its desaturation decays exponentially from its initial value (the arterial saturation, $S^{(a)}$ as $S^{(a)}C^{-\alpha t}$, so that the average capillary saturation is $\langle S^{(c)} \rangle = S^{(a)}(1-e^{-\alpha t^{(c)}})/(\alpha t^{(c)})$. The venous saturation is the final value at the end of the capillary compartment (i.e. $S^{(v)} = S^{(a)}e^{-\alpha t^{(c)}}$). This final concentration stays constant in the venous compartment since there is no oxygen diffusion from venous blood to tissue. The steady state arterial, capillary, and venous blood volumes ($CBV_0^{(a)}$, $\mathcal{F}^{(c)}CBV_0^{(c)}$, $CBV_0^{(v)}$, respectively where the reduced hemoglobin concentration in capillary blood is accounted for by the Fahraeus factor $\mathcal{F}^{(c)}$) specify the relative contributions of each compartment to the overall blood volume.

In FIG. 3, the overall model 310 is associated with a steady state ctHb parameter representing the blood concentration of hemoglobin. The arterial compartment 352 is associated with two steady state, baseline physiological parameters: $S^{(a)}$ which is the arterial hemoglobin saturation and $CBV_0^{(a)}$ which relates to baseline arterial cerebral blood volume. The capillary compartment 354 is associated with three steady state, baseline physiological parameters: $t^{(c)}$ which relates to capillary microvasculature blood transit time, $\mathcal{F}^{(c)}CBV_0^{(c)}$ which relates to baseline capillary blood volume, and a which is the rate constant for oxygen diffusion. The venous compartment 356 is associated with two steady state, baseline physiological parameters: $t^{(v)}$ which relates to venous microvasculature blood transit time and $CBV_0^{(v)}$ which relates to baseline venous blood volume.

2.2 Time-Varying Dynamic Functional Parameters

The time-varying dynamic functional parameters of the model are parameters that are expected to vary with time, for example, periodically in synchrony with a periodic activity (e.g., breathing, heartbeat, external induction protocol, etc.). In general, the arterial compartment contributes to dynamic changes only through variations in its blood volume, which can be described in terms of relative variations with respect to its steady state value: $cbv^{(a)}(t) = \Delta CBV^{(a)}(t)/CBV_0^{(a)}$.

In general, the capillary compartment does not contribute to blood volume changes because capillary recruitment/derecruitment and dilation/contraction are negligible in the brain. Contributions from the capillary compartment to dynamic changes are associated with changes in the rate constant a and in the capillary blood transit time $t^{(c)}$ (which directly affect the desaturation of capillary blood). The relationships between changes in a and changes in cerebral metabolic rate of oxygen (i.e. the amount of oxygen delivered per unit time per unit volume of tissue), and between changes in $t^{(c)}$ and changes in cerebral blood flow (i.e. the amount of blood flowing per unit time per unit volume of tissue) are:

$$cbf(t) = \frac{\Delta CBF(t)}{CBF_0} = -\frac{\Delta t^{(c)}}{t^{(c)}},$$

and:

$$cmro_2(t) = \frac{\Delta CMRO_2(t)}{CMRO_2|_0} = \frac{S^{(v)}}{\langle S^{(c)} \rangle}\frac{\Delta \alpha}{\alpha_0} + \left(1 - \frac{S^{(v)}}{\langle S^{(c)} \rangle}\right)\frac{\Delta t^{(c)}}{t^{(c)}}.$$

That is, the relative change in cerebral blood flow is equal and opposite to a relative change in the capillary transit time, and the relative change in metabolic rate of oxygen is determined by both a change in the rate constant of oxygen diffusion (for obvious reasons) and by a change in the capillary transit time (because an increase in the blood transit time results in an increase in the oxygen delivery to tissue).

In general, the venous compartment contributes to dynamic changes through variations in its blood volume, which can be described in terms of relative variations with respect to its steady state value: $cbv^{(v)}(t) = \Delta CBV^{(v)}(t)/CBV_0^{(v)}$. It also contributes through the way in which the hemoglobin saturation changes originating from the capillary compartment are propagated through the venous compartment over the venous blood transit time $t^{(v)}$. It is important to observe that, contrary to $t^{(c)}$, $t^{(v)}$ plays no role in the steady state conditions and it plays a more indirect role than $t^{(c)}$ in determining the hemoglobin saturation distribution in response to a perturbation: a change in $t^{(c)}$ directly changes the average capillary hemoglobin saturation, whereas a change in $t^{(v)}$ changes the average venous saturation only as a result of the propagation of the capillary saturation changes through the venous compartment.

In FIG. 3, the arterial component 352 is associated with a time-varying dynamic functional parameter, $cbv^{(a)}(t)$ which relates to variations in arterial compartment blood volume relative to the baseline arterial cerebral blood volume, $CBV_0^{(a)}$. The capillary compartment 354 is associated with two time-varying dynamic functional parameters: $cbf(t)$ which is related to variations in cerebral blood flow relative to a baseline cerebral blood flow, $CBF_0$ and $cmro_2(t)$ which is related to variations in metabolic rate of oxygen relative to a baseline metabolic rate of oxygen, $CMRO_{2|0}$. The venous compartment 356 is associated with a time-varying dynamic functional parameter $cbv^{(v)}(t)$ which is related to variations in venous compartment blood volume relative to the baseline venous cerebral blood volume, $CBV_0^{(v)}$.

3 Applications

As is noted above, the cerebral hemodynamic and oxygen supply modeling system 100 (see FIG. 1) can be used to infer hidden physiological baseline parameters (i.e., physiological parameters which remain constant over time) using a frequency-domain implementation (referred to as coherent hemodynamics spectroscopy) or to infer hidden dynamic functional parameters (i.e., parameters which vary over time) using a time-domain implementation. The following sections describe these two applications in detail.

3.1 Coherent Hemodynamics Spectroscopy

Coherent hemodynamics spectroscopy uses frequency resolved measurements of physiological signals that are representative of hemodynamic oscillations in test subject 104 to characterize tissue hemodynamics. The characterization of tissue hemodynamics afforded by coherent hemodynamics spectroscopy lends itself to the determination of relevant diagnostic physiological parameters. More generally coherent hemodynamics spectroscopy can yield robust measurements of spectral features of physiological signals (peak frequency, slope over a certain frequency band, frequency of zero-crossing, etc.) that may correlate with a given disease, functional state, or physiological condition.

Figure 4:
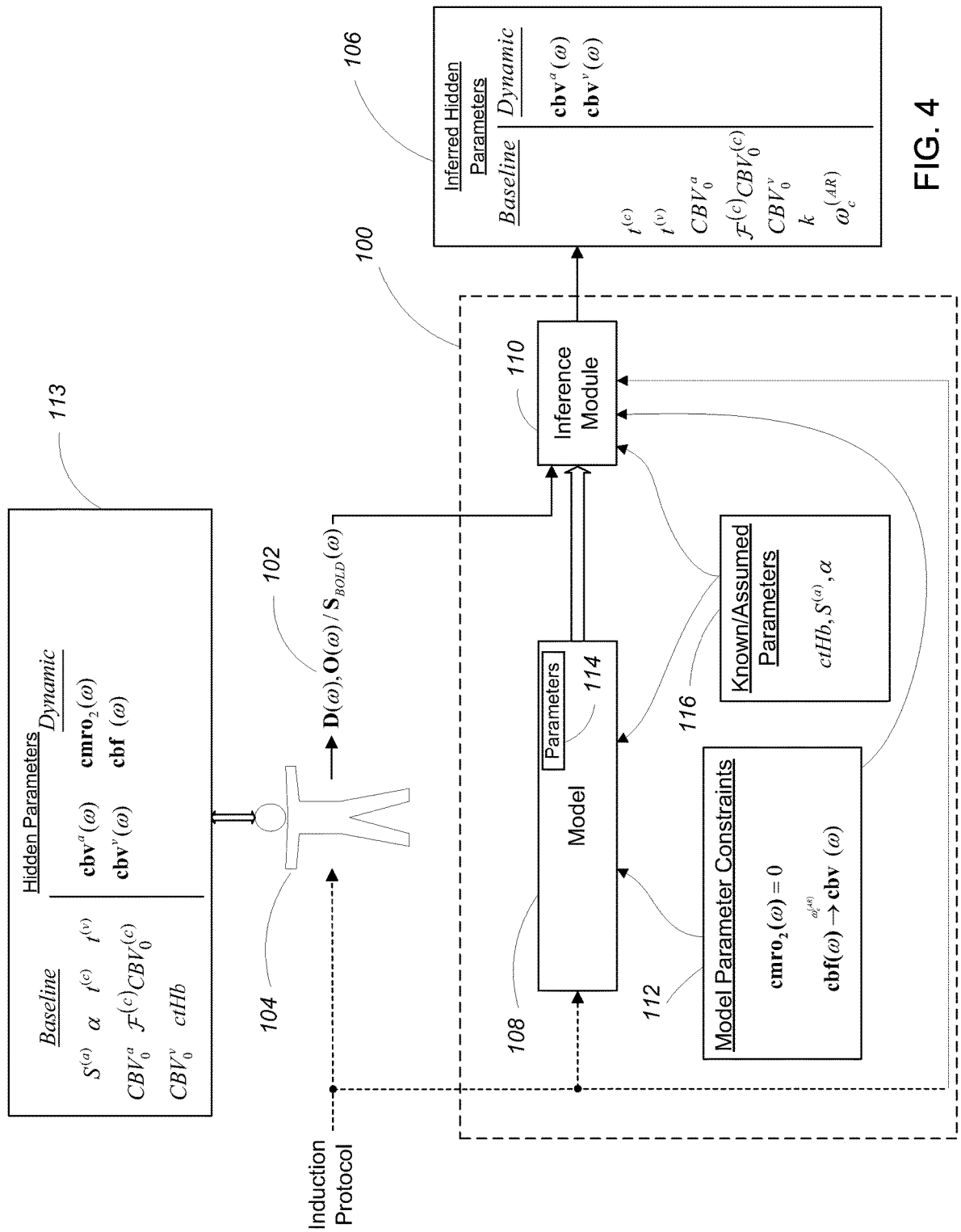
FIG. 4 is a cerebral hemodynamics and oxygen supply model based inference system configured for coherent hemodynamics spectroscopy.

Referring to FIG. 4, the cerebral hemodynamic and oxygen supply modeling system 100 of FIG. 1 is configured to perform coherent hemodynamics spectroscopy. Such a configuration of the system 100 is useful in cases where cerebral hemodynamics for a test subject 104 feature oscillations at specific frequencies or over certain frequency bands. Such oscillations may be spontaneous (e.g., arterial pulsation at ~1 Hz, respiration at ~0.3 Hz, low-frequency oscillations in the frequency band 0.05-0.15 Hz, etc.), or they may be induced by targeted induction protocols involving paced breathing or breath holding, inflation/deflation of a pneumatic cuff placed around a limb, tilt bed procedures, squat-stand maneuvers, modulation of fraction of inspired oxygen ($O_2$) or carbon dioxide ($CO_2$), etc. Such targeted induction protocols may be performed in a cyclic fashion, at a number of well-determined frequencies, or they may involve some temporal shape such as a step function in which the protocol applies a sudden change to the physiological system.

In both the case of spontaneous oscillations or induced oscillations, the cerebral hemodynamic and oxygen supply modeling system 100 performs a frequency based analysis of the physiological signals 102 to generate a frequency-resolved, or spectral representation of the oscillatory cerebral hemodynamics. If the hemodynamic oscillations feature a sufficiently high level of coherence, with a stable amplitude and phase, the cerebral hemodynamics and oxygen supply model is applicable and realizes the technique of Coherent Hemodynamics Spectroscopy (CHS). Note that this analysis is, in general, performed at multiple frequencies either in a combined operation, or by inducing each frequency in sequence.

Oscillations at a specific frequency $\omega$ are indicated with phasors (i.e. 2-dimensional vectors defined in terms of the amplitude and phase of the oscillations), so that the time-dependent quantities cbv(t), cbf(t), and $cmro_2$(t) are replaced by the corresponding phasors cbv ($\omega$), cbf($\omega$), and $cmro_2$ ($\omega$).

To configure the system 100 for coherent hemodynamics spectroscopy, three parameters are fixed as known/assumed parameters 116: cHtb, $S^{(a)}$ and $\alpha$. Furthermore, two model parameter constraints 112 are defined. The first constraint is that $cmro_2(\omega)=0$. This constraint is valid under conditions of spontaneous oscillations or protocols that do not affect the cerebral metabolic rate of oxygen. The second constraint comes from using a cerebral autoregulation model to introduce a relationship between the oscillations in cerebral blood flow and cerebral blood volume as follows:

$$cbf(\omega) = k \, \mathcal{H}_{HP}^{(AR)}(\omega, \omega_c) cbv(\omega)$$

where $\mathcal{H}_{HP}^{(AR)}(\omega, \omega_c)$ is an autoregulation (AR), high-pass (HP) transfer function given as:

$$\mathcal{H}_{HP}^{(AR)}(\omega) = \frac{1}{\sqrt{1 + \left(\frac{\omega_c^{(AutoReg)}}{\omega}\right)^2}} e^{i \tan^{-1}\left(\frac{\omega_c^{(AutoReg)}}{\omega}\right)}$$

where an autoregulation cutoff frequency ($\omega_c$) specifies the level of cerebral autoregulation, and k is the maximum amplitude ratio of flow-to-volume oscillations. Since, in this approach, $cmro_2(\omega)$ is set to 0, and cbf($\omega$) is replaced by an expression in terms of cbv($\omega$), there are two additional baseline parameters (k and $\omega_c$) describing cerebral autoregulation, and cbv($\omega$) (with contributions from $cbv^{(a)}(\omega)$ and $cbv^{(v)}(\omega)$) is the only frequency-dependent quantity left.

The model parameter constraints 112 and the known/assumed parameters 116 are used to configure the model 108 and the inference module 110. With the model 108 and the inference module 110 configured, the physiological signals 102 are measured from the test subject 104 and provided to the cerebral hemodynamic and oxygen supply modeling system 100 and subsequently to the inference module 110.

The inference module 110 processes the physiological signals 102 according to the model 108, the model parameter constraints 112, and the known/assumed parameters 116 to infer the unknown hidden physiological parameters. The inference module 110 does so by fitting the spectral representation of the measured physiological signals 102 to the hemodynamic model 108. Specifically, the fitting procedure performed by the inference module 110 is an established mathematical approach based on finding the optimal set of the unknown physiological parameters by minimizing a cost function ($\chi^2$) defined as the sum of the square of the residuals (i.e. the difference between the measured data and the model predictions). The fitting procedure uses the Jacobian matrix determined from the model structure, which is the matrix of partial derivatives of the measured signals (identified as $s_i$) with respect to the model parameters (identified as $p_j$). Using the above identifiers, the Jacobian matrix is expressed as:

$$J = \begin{pmatrix} \frac{\partial s_1}{\partial p_1} & \cdots & \frac{\partial s_1}{\partial p_n} \\ \vdots & \ddots & \vdots \\ \frac{\partial s_m}{\partial p_1} & \cdots & \frac{\partial s_m}{\partial p_n} \end{pmatrix}$$

The Jacobian matrix used to infer the hidden physiological parameters with Coherent Hemodynamics Spectroscopy (CHS) guides incremental adjustments of the set of parameters $p_j$ in order to achieve a suitable fit with the measured physiological signals $s_i$. The hemodynamic model 108 is used by the inference module 110 to determine the specific Jacobian matrix that relates the measured signals to the physiological parameters considered in coherent hemodynamics spectroscopy.

After the inference module 110 has applied the fitting procedure based on the Jacobian matrix, the inferred hidden parameters 106 are output from the system 100. As is evident from the figure, the steady state baseline hidden parameters inferred by the system 100 in its coherent hemodynamics spectroscopy configuration are: k, $\omega_c$, $t^{(c)}$, $t^{(v)}$, $CBV_0^{(a)}$, $\mathcal{F}^{(c)} CBV_0^{(c)}$ and $CBV_0^{(v)}$. The dynamic functional parameters inferred by the system 100 in its coherent hemodynamics spectroscopy configuration are: $cbv^{(a)}(\omega)$ and $cbv^{(v)}(\omega)$. Referring to FIG. 5, the list of steady state baseline physiological parameters and time-varying dynamic functional parameters considered by the system 100 when configured in coherent hemodynamics spectroscopy is summarized.

In some examples, the system 100 when configured for coherent hemodynamics spectroscopy is suitable for non-invasive measurement of cerebral autoregulation (i.e., the process that maintains a relatively constant cerebral blood flow over a range of cerebral perfusion pressures).

3.2 General Time-Varying Physiological Signals

Figure 6:
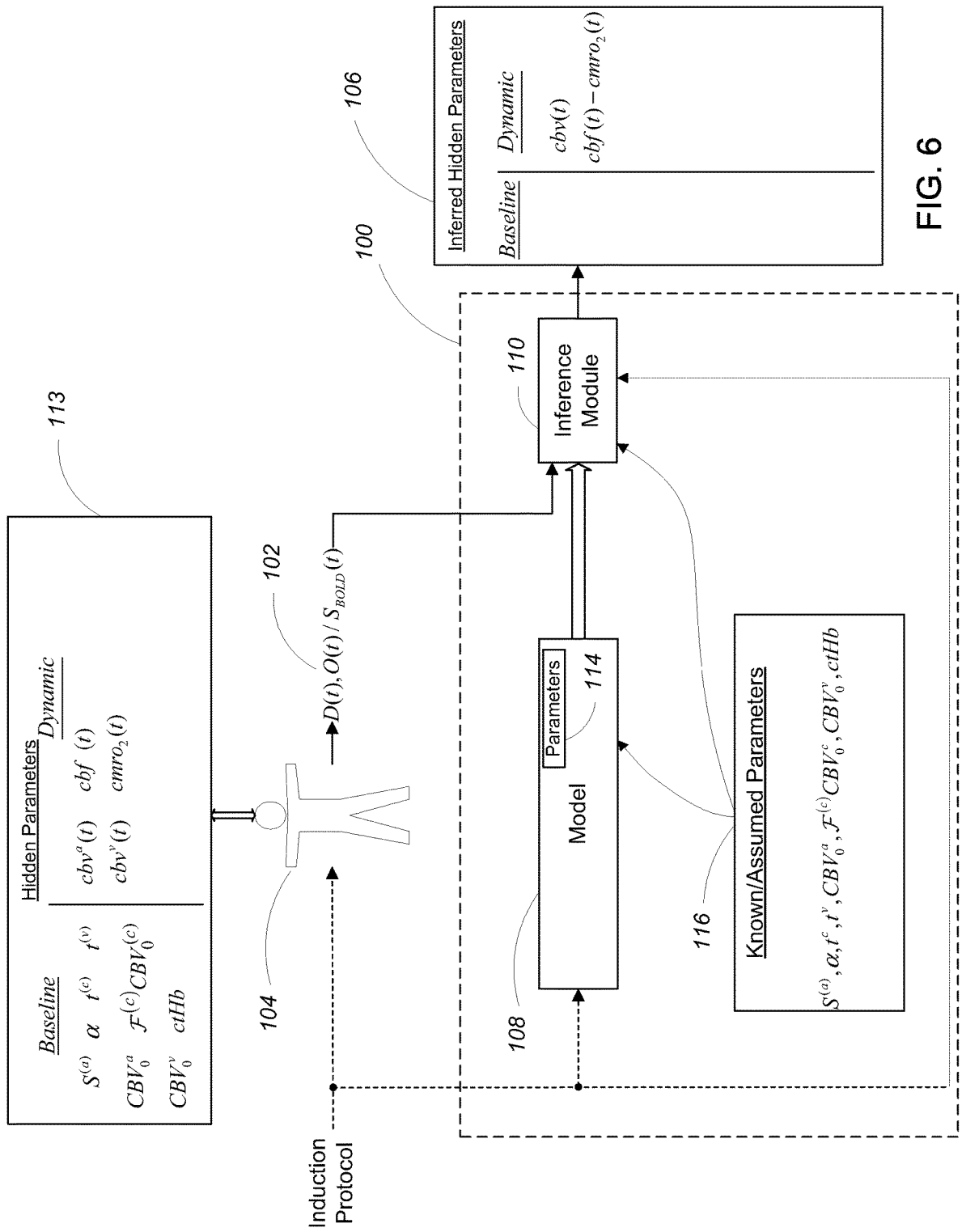
FIG. 6 is a cerebral hemodynamics and oxygen supply model based inference system configured for investigation of general time-varying signals.

Referring to FIG. 6, the cerebral hemodynamic and oxygen supply modeling system 100 of FIG. 1 is configured for application to any time-varying physiological signals to infer certain hidden, time-varying dynamic functional physiological parameters. In this configuration of the system 100, one does not have to make assumptions about the time-varying cerebral metabolic rate of oxygen (to allow for variable oxygen consumption such as the case of brain activation), cerebral blood flow and volume (to allow for more general conditions than the specific autoregulation condition used in the coherent hemodynamics spectroscopy configuration). That is, the configuration of the system 100 in FIG. 6 has no model parameter constraints 112. The system 100 does however have eight parameters fixed as known/assumed parameters 116: $S^{(a)}$, $\alpha$, $t^{(c)}$, $t^{(v)}$, $CBV_0^{(a)}$, $\mathcal{F}^{(c)} CBV_0^{(c)}$, $CBV_0^{(v)}$ and ctHb.

The known/assumed parameters 116 are used to configure the model 108 and the inference module 110. With the model 108 and the inference module 110 configured, the physiological signals 102 are measured from the test subject 104 and provided to the cerebral hemodynamic and oxygen supply modeling system 100 and subsequently to the inference module 110.

The inference module 110 processes the physiological signals 102 according to the model 108 and the known/assumed parameters 116 to infer the unknown hidden physiological parameters. The inference module does so using a two-step process. In the first step the inference module 110 directly determines cbv(t) by the measured change in total hemoglobin concentration $(\Delta T/T_0 = \Delta D/D_0 + \Delta O/O_0)$ as shown by Eq. (A.3) in the Appendix section below. In the second step, the inference module 110 translates the convolution products in the time-domain model equations [indicated with the symbol * in Eqs. (A.1) and (A.2) in the Appendix] into regular products by Fourier transformation of these equations. In practical terms, this step requires that the measured physiological signals 102 be first Fourier transformed, so that the difference between the time-varying blood flow and metabolic rate of oxygen $[\widetilde{cbf}(\omega) - \widetilde{cmro_2}(\omega)]$ is determined [as shown by Eq. (A.14) in the Appendix]. An inverse Fourier transformation finally yields the difference between the actual time-varying physiological quantities $cbf(t) - cmro_2^{(t)}$.

As is evident from FIG. 6, the parameters inferred by the system 100 in its general time-varying physiological signals configuration are the time-varying dynamic functional parameters: cbv(t) and $cbf(t) - cmro_2^{(t)}$. Referring to FIG. 7, the list of steady state baseline physiological parameters and time-varying dynamic functional parameters considered by the system 100 when configured in its general time-varying signals configuration is summarized.

4 Alternatives

As is noted above, while the above example generally relates to the use of fNIRS measurements as inputs to the model, the model can also be used with measurements from other types of sensors such as fMRI measurements. In the case of fMRI, the sensor is sensitive only to the paramagnetic deoxygenated form of hemoglobin. Thus, for fMRI, additional parameters such as blood pressure or cerebral blood flow may be required for proper operation of the model.

In some examples, the cerebral hemodynamics and oxygen supply model can be used in conjunction with the autoregulation model to predict the parameters of the autoregulation model. For example, the cutoff frequency of the high-pass autoregulation model can be predicted.

In some examples, the cerebral hemodynamics and oxygen supply model can be used to measure cerebrovascular reactivity, which is a measure of the compensatory dilatory or constrictive capacity of the cerebral microvasculature in response to physiological challenges such as an increase in the concentration of carbon dioxide ($CO_2$) in blood.

More generally, the systems described above can serve as a framework for studies of cerebral hemodynamics and oxygenation. By properly designing protocols involving periodic brain stimulation, physiological challenges, or other kinds of active or passive physical maneuvers, one can predict physiological characteristics which can not be directly measured.

In some examples, different hemodynamic models may be used in the systems described above. The idea of characterizing tissue hemodynamics by performing frequency-resolved measurements (i.e. spectroscopy) of coherent oscillations will still apply to such models.

While the above description describes the induction of coherent oscillations (i.e., by periodic protocols), in some examples, coherent oscillations may also occur spontaneously. The system described above can operate on spontaneous coherent oscillations as well.

While the systems described above all employ models of physiological systems, in some examples, no model is required by a coherent hemodynamics spectroscopy system. For example, such a system can include a coherent hemodynamics spectroscopy analysis module that receives only two inputs: the frequency-resolved spectral representations of the measured signals and knowledge of a given set of physiological, pathological, or functional states. From those two inputs, the coherent hemodynamics spectroscopy analysis module can determine whether there are correlations between spectral features of the measured signals and the physiological/pathological/functional conditions. Any determined correlations can be then used as diagnostic or functional measures of the associated physiological/pathological/functional condition. In this case, the coherent hemodynamics spectroscopy module would receive solely the input of the frequency-resolved spectral representations of the measured hemoglobin concentration and oxygenation signals, and would provide a diagnostic, metabolic, or functional measure on the basis of the spectral features of the measured concentration and oxygenation signals.

5 Implementations

Systems that implement the techniques described above can be implemented in software, in firmware, in digital electronic circuitry, or in computer hardware, or in combinations of them. The system can include a computer program product tangibly embodied in a machine-readable storage device for execution by a programmable processor, and method steps can be performed by a programmable processor executing a program of instructions to perform functions by operating on input data and generating output. The system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

In some examples, the physiological signals are measured from the test subject using near-infrared spectroscopy (NIRS) or functional NIRS (fNIRS) techniques. In some examples, the physiological signals are measured from the test subject using functional magnetic resonance imaging techniques (fMRI).

In some examples, subjecting an organism including the physiological system to a periodic protocol or a temporal perturbation is done by means of equipment such as an automatic pneumatic cuff inflation system, a computer-controlled gas mixer, a tilt bed, active/passive exercise machines, brain activation systems or protocols, etc.

It is understood that the foregoing description is intended to illustrate and not to limit the scope of the invention, which is defined by the scope of the appended claims. Other embodiments are within the scope of the appended claims.

6 Appendix

Mathematical Expressions of the Cerebral Hemodynamic and Oxygen Supply Model

6.1 Time-Domain Equations

The hemodynamic model relates the time-dependent concentrations of deoxy-hemoglobin [D(t)], oxy-hemoglobin [O(t)], and total hemoglobin [T(t)] in brain tissue, as well as the fMRI BOLD signal [$S_{BOLD}$(t)], to perturbations in the arterial and venous blood volumes [$cbv^{(a)}$(t) and $cbv^{(v)}$(t), respectively], and the difference between perturbations in the cerebral blood flow [$cbf^{(t)}$] and the cerebral metabolic rate of oxygen [$cmro_2$(t)]. The specific equations are:

$$D(t) = ctHb[(1 - S^{(a)})CBV_0^{(a)} + (1 - \langle S^{(c)} \rangle)\mathcal{F}^{(c)}CBV_0^{(c)} + (1 - S^{(v)})CBV_0^{(v)}] + + ctHb[(1 - S^{(a)})CBV_0^{(a)}cbv^{(a)}(t) + (1 - S^{(v)})CBV_0^{(v)}cbv^{(v)}(t)] + - ctHb\left[\frac{\langle S^{(c)} \rangle}{S^{(v)}}(\langle S^{(c)} \rangle - S^{(v)})\mathcal{F}^{(c)}CBV_0^{(c)}h_{RC-LP}^{(c)}(t) + (S^{(a)} - S^{(v)})CBV_0^{(v)}h_{G-LP}^{(v)}(t)\right] * [cbf(t) - cmro_2(t)]$$
(A.1)

$$O(t) = ctHb[S^{(a)}CBV_0^{(a)} + \langle S^{(c)} \rangle \mathcal{F}^{(c)}CBV_0^{(c)} + S^{(v)}CBV_0^{(v)}] + ctHb[S^{(a)}\Delta CBV^{(a)}(t) + S^{(v)}\Delta CBV^{(v)}(t)] + + ctHb\left[\frac{\langle S^{(c)} \rangle}{S^{(v)}}(\langle S^{(c)} \rangle - S^{(v)})\mathcal{F}^{(c)}CBV_0^{(c)}h_{RC-LP}^{(c)}(t) + (S^{(a)} - S^{(v)})CBV_0^{(v)}h_{G-LP}^{(v)}(t)\right] * [cbf(t) - cmro_2(t)]$$
(A.2)

$$T(t) = ctHbCBV_0[1 + cbv(t)]$$
(A.3)

$$S_{BOLD}(t) = CBV_0\left[3.4\left(1 - \frac{D(t)}{D_0}\right) - \frac{(1 - S^{(a)})cbv^{(a)}(t) + (1 - S^{(v)})cbv^{(v)}(t)}{3 - S^{(a)} - \langle S^{(c)} \rangle - S^{(v)}}\right]$$
(A.4)

where ctHb is the concentration of hemoglobin in blood, $CBV_0$ is the baseline blood volume, $\mathcal{F}^{(c)}$ is the ratio of capillary to large vessel hematocrit (Fahraeus factor), S is the blood oxygen saturation, and superscripts (a), (c), (v) indicate the arterial, capillary, and venous compartments, respectively. The * operator indicates a convolution product. The impulse responses associated with the capillary [$h_{RC-LP}^{(c)}$(t)] and venous [$h_{G-LP}^{(v)}$(t)] compartments are given by:

$$h_{RC-LP}^{(c)}(t) = H(t)\frac{e}{t^{(c)}}e^{-et/t^{(c)}}$$
(A.5)

$$h_{G-LP}^{(v)}(t) = \frac{1}{0.6(t^{(c)} + t^{(v)})}e^{-\pi[t - 0.5(t^{(c)} + t^{(v)})]^2 / [0.6(t^{(c)} + t^{(v)})]^2}$$
(A.6)

where $t^{(c)}$ and $t^{(v)}$ are the blood transit times in the capillary and venous compartments, respectively, and H(t) is the Heaviside unit step function (H(t)=0 for t<0; H(t)=1 for t≥0).

6.2 Frequency-Domain Equations

The hemodynamic model equations [Eqs. (A.1)-(A.4)] can be expressed in the frequency domain by replacing time-varying quantities with 2-dimensional phasors (identified in bold face) defined in terms of the amplitude and phase of the associated oscillations at frequency ω. The frequency-domain equations are:

$$D(\omega) = ctHb[(1 - S^{(a)})CBV_0^{(a)}cbv^{(a)}(\omega) + (1 - S^{(v)})CBV_0^{(v)}cbv^{(v)}(\omega)] + - ctHb\left[\frac{\langle S^{(c)} \rangle}{S^{(v)}}(\langle S^{(c)} \rangle - S^{(v)})\mathcal{F}^{(c)}CBV_0^{(c)}\mathcal{H}_{RC-LP}^{(c)}(\omega) + (S^{(a)} - S^{(v)})CBV_0^{(v)}\mathcal{H}_{G-LP}^{(v)}(\omega)\right][cbf(\omega) - cmro_2(\omega)]$$
(A.7)

$$O(\omega) = ctHb[S^{(a)}CBV_0^{(a)}cbv^{(a)}(\omega) + S^{(v)}CBV_0^{(v)}cbv^{(v)}(\omega)] + + ctHb\left[\frac{\langle S^{(c)} \rangle}{S^{(v)}}(\langle S^{(c)} \rangle - S^{(v)})\mathcal{F}^{(c)}CBV_0^{(c)}\mathcal{H}_{RC-LP}^{(c)}(\omega) + (S^{(a)} - S^{(v)})CBV_0^{(v)}\mathcal{H}_{G-LP}^{(v)}(\omega)\right][cbf(\omega) - cmro_2(\omega)]$$
(A.8)

$$T(\omega) = ctHb[CBV_0^{(a)}cbv^{(a)}(\omega) + CBV_0^{(v)}cbv^{(v)}(\omega)]$$
(A.9)

$$S_{BOLD} = CBV_0\left[3.4\left(1 - \frac{D(\omega)}{D_0}\right) - \frac{(1 - S^{(a)})cbv^{(a)} + (1 - S^{(v)})cbv^{(v)}}{3 - S^{(a)} - \langle S^{(c)} \rangle - S^{(v)}}\right]$$
(A.10)

where $\mathcal{H}_{RC-SP}^{(c)}(\omega)$ and $\mathcal{H}_{G-LP}^{(v)}(\omega)$ are complex transfer function given by:

$$\mathcal{H}_{RC-LP}^{(c)}(\omega) = \frac{1}{\sqrt{1+\left(\frac{\omega t^{(c)}}{e}\right)^2}} e^{-i\tan^{-1}\left(\frac{\omega t^{(c)}}{e}\right)} \quad (A.11)$$

$$\mathcal{H}_{G-LP}^{(v)}(\omega) = e^{-\frac{\ln 2}{2}[\omega 0.281(t^{(c)}+t^{(v)})]^2} e^{-i\omega 0.5(t^{(c)}+t^{(v)})}. \quad (A.12)$$

The cerebral autoregulation transfer function used in CHS is given by:

$$\mathcal{H}_{HP}^{(AR)}(\omega) = \frac{1}{\sqrt{1+\left(\frac{\omega_c^{(AutoReg)}}{\omega}\right)^2}} e^{i\tan^{-1}\left(\frac{\omega_c^{(AutoReg)}}{\omega}\right)} \quad (A.13)$$

The following equation provides the relationship between the Fourier transforms of cbf(t) and cmro$_2$(t), and the Fourier transforms of the oxy- and deoxy-hemoglobin concentration changes [$\Delta O(t)$ and $\Delta D(t)$]:

$$\widetilde{cbf}(\omega) - \widetilde{cmro}_2(\omega) = \frac{\frac{\Delta O(\omega) - \Delta D(\omega)}{T_0} - (2S^{(a)}-1)\frac{CBV_0^{(a)}}{CBV_0}\widetilde{cbv}^{(a)}(\omega) - (2S^{(v)}-1)\frac{CBV_0^{(v)}}{CBV_0}\widetilde{cbv}^{(v)}(\omega)}{2\left[\frac{\langle S^{(c)}\rangle}{S^{(v)}}(\langle S^{(c)}\rangle - S^{(v)})\mathcal{F}^{(c)}\frac{CBV_0^{(c)}}{CBV_0}\mathcal{H}_{RC-LP}^{(c)}(\omega) + (S^{(a)} - S^{(v)})\frac{CBV_0^{(v)}}{CBV_0}\mathcal{H}_{G-LP}^{(v)}(\omega)\right]}, \quad (A.14)$$

where $T_0 = ctHb\, CBV_0$ is the baseline total concentration of hemoglobin, and the tildes indicate Fourier transformation. Equation (A.14) shows how the Fourier transforms of the measured changes $\Delta D(t)$ and $\Delta O(t)$ (i.e. $\widetilde{\Delta D}(\omega)$ and $\widetilde{\Delta O}(\omega)$) can be translated into the difference of the Fourier transforms of cbf(t) and cmro$_2$(t) [i.e. $\widetilde{cbf}(\omega)\; \widetilde{cmro}_2(\omega)$].

What is claimed is:

1. A method comprising:
 connecting a test subject to a modeling system that implements a hemodynamic model, the modeling system being a cerebral hemodynamic and oxygen supply modeling system,
 using the modeling system, inferring parameters of a physiological system of the test subject, and
 making information representative of said inferred parameters available to medical professionals for use as a basis for diagnosing or monitoring the test subject,
 wherein inferring the parameters comprises
  measuring signals from the test subject's physiological system, said signals being physiological signals, wherein among the signals are signals that are coherent oscillations from the test subject's physiological system, said coherent oscillations being at a plurality of frequencies,
  causing the modeling system to use the hemodynamic model to infer parameters of the test subject's physiological system from at least one of the measured signals,
 wherein the hemodynamic model defines a relationship between the measured signals and the parameters,
 wherein the hemodynamic model is a multiple vascular-compartment hemodynamic model,
 wherein the multiple vascular compartments comprise a capillary compartment,
 wherein the hemodynamic model is based on an average time spent by blood in one or more vascular compartments and a rate constant of oxygen diffusion, and
 wherein the parameters are selected from the group consisting of a maximum amplitude ratio of flow-to-volume oscillations, hemoglobin concentration in blood, arterial saturation, rate constant for oxygen diffusion, capillary blood transit time, venous blood transit time, arterial blood volume, capillary blood volume, cutoff frequency for autoregulation, and blood volume phasor,
 wherein inferring the parameters further comprises inferring the parameters based on one or more representations of the coherent oscillations,
 wherein the representations are selected from the group consisting of spectral representations of the coherent oscillations and temporal representations of the coherent oscillations, and
 wherein inferring the parameters based on one or more representations of the coherent oscillations comprises fitting representations of the coherent oscillations to the hemodynamic model.

2. The method of claim 1, wherein the coherent oscillations at the plurality of frequencies in the physiological system occur spontaneously.

3. The method of claim 1, further comprising inducing the coherent oscillations by subjecting said test subject to a plurality of periodic protocols, each periodic protocol of the plurality of periodic protocols having a period corresponding to one of the frequencies of the plurality of frequencies.

4. The method of claim 3, wherein the plurality of periodic protocols includes one or more of: paced breathing, repeated active exercise maneuvers, repeated passive exercise maneuvers, periodic tilting bed procedures, cyclic inflation and deflation of a pneumatic device, cyclic brain activation, and modulation of a fraction of inspired oxygen (FiO2) or carbon dioxide (FiCO2).

5. The method of claim 1, further comprising inducing the coherent oscillations by subjecting the test subject to a perturbation.

6. The method of claim 5, wherein subjecting the test subject to a perturbation comprises causing a sudden change to be applied to the test subject.

7. The method of claim 1, wherein the signals include time-varying physiological signals and wherein inferring parameters includes inferring time-varying parameters.

8. The method of claim 1, wherein measuring signals comprises carrying out functional near-infrared spectroscopy to measure said signals.

9. The method of claim 1, wherein measuring signals from the test subject's physiological system comprises using functional magnetic resonance imaging (fMRI) techniques to measure said signals.

10. The method of claim 1, wherein the physiological system is a brain autoregulation system.

11. The method of claim 1, wherein the physiological system is a cerebrovascular reactivity system.

12. The method of claim 1, wherein the physiological system is a cerebral blood volume system.

13. The method of claim 1, wherein the physiological system is a cerebral blood flow system.

14. The method of claim 1, wherein the physiological system is a cerebral metabolic rate of oxygen system.

15. The method of claim 1, wherein the one or more representations of the coherent oscillations include temporal representations of the coherent oscillations.

16. The method of claim 1, wherein the one or more representations of the coherent oscillations include spectral representations of the coherent oscillations.

17. The method of claim 1, wherein making information representative of said inferred parameters available to medical professionals for use as a basis for diagnosing or monitoring the test subject comprises presenting at least some of the parameters to a clinician.

18. The method of claim 1, wherein measuring signals comprises carrying out near-infrared spectroscopy to measure said signals.

19. A method comprising:
connecting a test subject to a modeling system that implements a hemodynamic model,
using the modeling system, inferring parameters of the test subject's physiological system, and
making information representative of said inferred parameters available to medical professionals for use as a basis for diagnosing or monitoring the test subject,
wherein the modeling system is a cerebral hemodynamic and oxygen supply modeling system,
wherein inferring parameters of the physiological system comprises
obtaining measurements of physiological signals from the test subject's physiological system, wherein the measurements include measurements of coherent oscillations from the physiological system, said coherent oscillations being at a plurality of frequencies,
determining one or more representations of the coherent oscillations, and
inferring the parameters based on previously determined correlations between the parameters and individual features of the one or more representations of the coherent oscillations,
wherein inferring the parameters comprises inferring the parameters based on the one or more representations of the coherent oscillations,
wherein the representations are selected from the group consisting of spectral representations of the coherent oscillations and temporal representations of the coherent oscillations,
wherein inferring the parameters based on the one or more representations of the coherent oscillations further comprises fitting representations of the coherent oscillations to the hemodynamic model, and
wherein the parameters are selected from the group consisting of a maximum amplitude ratio of flow-to-volume oscillations, hemoglobin concentration in blood, arterial saturation, rate constant for oxygen diffusion, capillary blood transit time, venous blood transit time, arterial blood volume, capillary blood volume, cutoff frequency for autoregulation, and blood volume phasor.

20. The method of claim 19, wherein the coherent oscillations at the plurality of frequencies in the physiological system occur spontaneously.

21. The method of claim 19, further comprising inducing the coherent oscillations by subjecting the test subject to a plurality of periodic protocols, each periodic protocol of the plurality of periodic protocols having a period corresponding to one of the frequencies of the plurality of frequencies.

22. The method of claim 21 wherein the plurality of periodic protocols includes one or more of: paced breathing, repeated active exercise maneuvers, repeated passive exercise maneuvers, periodic tilting bed procedures, cyclic inflation and deflation of a pneumatic device, cyclic brain activation, and modulation of a fraction of inspired oxygen (FiO2) or carbon dioxide (FiCO2).

23. The method of claim 19, further comprising inducing the coherent oscillations by subjecting the test subject to a perturbation.

24. The method of claim 23, wherein subjecting the test subject to a perturbation comprises causing a sudden change to be applied to said test subject.

25. The method of claim 19, wherein the one or more representations of the coherent oscillations include temporal representations of the coherent oscillations.

26. The method of claim 19, wherein the one or more representations of the coherent oscillations include spectral representations of the coherent oscillations.

27. An apparatus comprising a modeling system that implements a hemodynamic model, said modeling system being a cerebral hemodynamic and oxygen supply modeling system that implements a multiple vascular compartment hemodynamic model, said modeling system comprising:
a measurement module for measuring signals from a physiological system, said signals being physiological signals, wherein among the signals are signals that are coherent oscillations at a plurality of frequencies and
an inference module for inferring parameters of said physiological system from said measured signals, wherein said hemodynamic model defines a relationship between said signals and said parameters,
wherein said hemodynamic model is based on an average time spent by blood in one or more vascular compartments and a rate constant of oxygen diffusion,
wherein said vascular compartments include a capillary compartment, wherein said parameters are selected from the group consisting of a maximum amplitude ratio of flow-to-volume oscillations, hemoglobin concentration in blood, arterial saturation, rate constant for oxygen diffusion, capillary blood transit time, venous blood transit time, arterial blood volume, capillary blood volume, cutoff frequency for autoregulation, and a blood volume phasor,
wherein the inference module is configured to infer the parameters based on one or more representations of the coherent oscillations,
wherein the representations are selected from the group consisting of spectral representations of the coherent oscillations and temporal representations of the coherent oscillations, and
wherein inferring the parameters based on one or more representations of the coherent oscillations comprises fitting representations of the coherent oscillations to the hemodynamic model.

* * * * *